United States Patent
Dupuis et al.

(10) Patent No.: US 7,888,524 B2
(45) Date of Patent: Feb. 15, 2011

(54) PROCESS FOR PREPARING SULFURIC MONOESTERS FROM AMINO ALKANOLS

(75) Inventors: Jacques Dupuis, Ketsch (DE); Reinhard Hoffmann, Hanhofen (DE); Ekhard Winkler, Mutterstadt (DE); Manfred Winter, Dittelsheim-Hessloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 309 days.

(21) Appl. No.: 12/095,234

(22) PCT Filed: Nov. 23, 2006

(86) PCT No.: PCT/EP2006/068842

§ 371 (c)(1),
(2), (4) Date: May 28, 2008

(87) PCT Pub. No.: WO2007/063032

PCT Pub. Date: Jun. 7, 2007

(65) Prior Publication Data

US 2008/0319215 A1    Dec. 25, 2008

(30) Foreign Application Priority Data

Dec. 2, 2005    (DE) .................. 10 2005 057 897

(51) Int. Cl.
*C07C 305/00*    (2006.01)
(52) U.S. Cl. ............................................ 558/29
(58) Field of Classification Search ............ 558/29
See application file for complete search history.

(56) References Cited

U.S. PATENT DOCUMENTS 4,330,480 A * 5/1982 Hertel et al. .................. 558/29
6,073,643 A   6/2000 Zheng

FOREIGN PATENT DOCUMENTS

DE    28 40 554 A1    3/1980
DE    101 24 300 A1   11/2002

* cited by examiner

*Primary Examiner*—Rei-tsang Shiao
(74) *Attorney, Agent, or Firm*—Oblon, Spivak, McClelland, Maier & Neustadt, L.L.P.

(57) ABSTRACT

Process for the preparation of sulfuric acid monoesters of aminoalkanols by reacting sulfuric acid with aminoalkanols and removing the water forming in the reaction from the reaction mixture, sulfuric acid and at least one aminoalkanol being mixed and the hot reaction mixture forming being passed with turbulent flow into a container and being quenched therein with a fluid.

15 Claims, No Drawings

PROCESS FOR PREPARING SULFURIC MONOESTERS FROM AMINO ALKANOLS

The invention relates to a process for the preparation of sulfuric acid monoesters of aminoalkanols by reacting sulfuric acid with aminoalkanols and removing the water forming in the reaction from the reaction mixture.

Sulfuric acid monoesters of aminoalkanols are intermediates. Thus, for example, the sulfuric acid monoester of 2-aminoethanol is used as a starting material in the industrial production of ethylenimine. Sulfuric acid monoesters of aminoalkanols are prepared by the process of DE-A 28 40 554 by simultaneous addition of aminoalkanols and sulfuric acid to a suspending medium boiling in the range from 70 to 150° C., such as octane, with paramixing, distilling off of the water forming in the reaction and, if appropriate, water fed in with the starting materials, together with a part of the suspending medium, as an azeotrope, removal of the water and recycling of the suspending medium into the reaction mixture, the suspending medium distilled off being replaced by fresh suspending medium, which is introduced in gaseous form, for example at a temperature of from 110 to 200° C., into the reaction mixture. The process has a plurality of disadvantages. It has, for example, a high energy requirement and requires complicated apparatus for the storage and working-up of the suspending medium. Moreover, the kettles must be cleaned at certain intervals in order to remove caked sulfuric acid monoesters.

DE-A 101 24 300 discloses a process for the preparation of sulfuric acid monoesters of aminoalkanols, sulfuric acid and aminoalkanols being allowed to react in the absence of conventional suspending media in a fluidized bed and water being distilled off from the reaction mixture. The temperature in the fluidized bed is in general from 140 to 160° C., but may also be up to 250° C. The apparatuses suitable for this purpose are complicated and expensive.

It is the object of the invention to provide an improved process for the preparation of sulfuric acid monoesters of aminoalkanols which has a lower energy requirement than the known processes and gives a higher space-time yield.

The object is achieved, according to the invention, by a process for the preparation of sulfuric acid monoesters of aminoalkanols by reacting sulfuric acid with aminoalkanols and removing the water forming in the reaction from the reaction mixture, if sulfuric acid and at least one aminoalkanol are mixed and the hot reaction mixture forming is passed with turbulent flow into a container and quenched therein with a fluid. The fluid is preferably an aqueous medium.

The process according to the invention is preferably carried out continuously. Diluents or suspending media are not required in the process according to the invention. This results in advantages in the working-up of the sulfuric acid monoester. The concentration of the sulfuric acid used in the process is, for example, from 90 to 100% by weight, in general from 96 to 98% by weight. However, it is also possible to use sulfuric acid which contains excess sulfur trioxide, so-called fuming sulfuric acid, or to carry out the esterification of the aminoalkanols with sulfur trioxide.

In the process according to the invention, all aminoalkanols can be esterified with sulfuric acid or sulfur trioxide. Aminoalkanols may be characterized, for example, with the aid of the following formula:

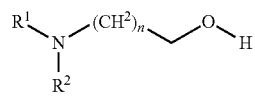

where the substituents $R^1$ and $R^2$ are identical or different and are hydrogen, aliphatic substituents which may be straight-chain, branched and/or cyclic and have 1 to 10 carbon atoms, substituted aliphatic radicals whose substituents are inert under the reaction conditions, and heterocycloaliphatic radicals having 3 to 6 carbon atoms, and n is from 1 to 10, preferably from 1 to 3, particularly preferably 2.

Examples of such aminoalkanols are ethanolamines, such as monoethanolamine (2-aminoethanol), diethanolamine and triethanolamine, isopropanolamine, N-isopropylethanolamine, N-cyclohexylethanolamine, N-cyclooctylethanolamine, 3-aminopropanol and N-cyclooctylisopropanolamine. It is also possible to use mixtures of aminoalcohols. The use of monoethanolamine as the aminoalcohol is particularly preferred.

The molar ratio of sulfuric acid to aminoalkanol is, for example, from 1:1.5 to 1:0.5, preferably from 1:1 to 1:0.9. In most cases, the two reactants are reacted in equimolar amounts. The temperature of the starting materials which are reacted with one another generally corresponds to ambient temperature. It is, for example, in the range from 5 to 30° C., preferably from 15 to 25° C. Sulfuric acid and at least one aminoalkanol are combined in a mixing zone, for example in a mixing chamber, or mixed with the aid of a multi-material nozzle. A spontaneous reaction occurs, which leads to a sharp temperature increase of the reaction mixture. The temperature increase relative to the temperature of the reactant is at least 200° C., for example from 250 to 300° C.

For example, it is possible to adopt a procedure in which sulfuric acid and at least one aminoalcohol are pumped into a mixing chamber separately from one another, in parallel, in opposite directions or at any desired angle, preferably from 30 to 90° C. However, the two components can also be combined with the aid of a multi-material nozzle, for example a binary nozzle, in a mixing zone or a mixing chamber. Owing to the highly exothermic reaction, a very sharp temperature increase incurs, which results in the reaction product being obtained in liquid form and in the water forming during the esterification vaporizing spontaneously. The temperature in the reaction zone is at least 220° C., preferably more than 250° C. For example, it is in the range from 260 to 300° C. It can, for example, be controlled by metering of fluid into the mixing zone or cooling or heating the mixing zone with the aid of a heat-transfer agent. A further possibility for temperature control is to preheat or cool one or more feeds.

The reaction mixture is passed from the reaction zone through at least one tube into a container in which it is quenched (i.e. quenched with a cold fluid) in order to condense the steam formed in the reaction, and, if required, the melt is crystallized or is dissolved in a solvent, such as water or aqueous base. The diameter of the tube is designed so that the reaction mixture is passed with turbulent flow into the downstream container. The turbulent flow ensures further paramixing of the reactants. For example, the reaction mixture can be passed through a tube having a diameter of at least 0.5 mm, for example a diameter in the range from 0.5 to 1000 mm, preferably from 1 to 200 mm, into a container and the reaction mixture can be quenched therein with a fluid, preferably an aqueous medium. The tube or the tube bundle may be straight or helical. The tube or tube bundle can be surrounded by a heat-transfer medium so that it is possible to withdraw heat from, or supply heat to, the reaction mixture. Direct electrical heating is also possible.

In a preferred embodiment of the invention, the tube has a smaller diameter at the beginning, i.e. at the point of departure from the mixing chamber to the quench container, than at the tube end which enters the quench container. For example, the tube diameter of a laboratory apparatus is 1 mm at the beginning of the tube and 5 mm at the end of the tube. The transition to a larger diameter may take place continuously or stepwise in segments whose diameter increases in each case, for example, by 1 mm. Particularly advantageous is an arrangement in which a tube whose cross section widens from top to bottom has a helical form.

Particularly thorough mixing of the reactants takes place in the helical tubes. As a result of the water which forms in the reaction and spontaneously vaporizes, the reaction mixture passes at very high velocity into the quench container. The velocity is, for example, at least 10 m/s, for example from 80 to 240 m/s and not more than about 500 m/s.

In a further development of the process according to the invention, the tube which leads from the mixing chamber to the quench container is designed so that it has a diameter which is a factor from 2 to 1000, preferably from 10 to 200, greater at the entrance into the quench container than at the exit of the mixing chamber. In another development of the invention, the reaction mixture is first passed through a tube into a container in which it is let down and thereafter passes into the quench container. The tube which leads from the mixing chamber to the flash container may have a constant diameter or may widen toward the flash container, as described above. It may be straight, or, preferably helical.

After leaving the tube, the hot reaction mixture is preferably quenched with a cold fluid. For example an aqueous medium, which may be pure water or an aqueous base, is used for the quenching. The temperature of the quench liquid may be, for example, from −10 to 80° C., in particular from 20 to 50° C. The quench liquid is usually sprayed onto the reaction mixture emerging from the tube or tube bundle, so that the steam is condensed as rapidly as possible. The sulfuric acid monoesters of aminoalkanols are liquid under the reaction conditions. They are obtained in the form of drops in the quench container. In addition to water, aqueous solutions of sodium hydroxide, of potassium hydroxide or of another base may be used as quench liquid. The corresponding salts of sulfuric acid monoesters, which are required, for example, for the synthesis of ethylenimine, are then obtained.

During continuous operation of the plant, the quench liquid is also fed continuously into the quench container. In order to prepare, for example, the sodium salts of sulfuric acid monoesters of aminoalkanols in a continuous procedure, a dilute aqueous sodium hydroxide solution is metered continuously into the quench circulation before the quenching of the reaction mixture and an aqueous solution of the sodium salt of sulfuric acid monoester of aminoalkanols is removed from the quench circulation after leaving the quench container. The amount of aqueous sodium hydroxide solution which is fed to the quench circulation can be controlled with the aid of the pH of the quench liquid. In the steady state, the quench liquid then contains not only sodium hydroxide solution but also, in dissolved form, the sodium salt of the sulfuric acid monoester of the aminoalkanols used in each case.

A process variant in which the reaction of sulfuric acid with aminoalkanols is carried out under reduced pressure, for example at absolute pressures of from 1 to 200 mbar, preferably from 15 to 50 mbar, is particularly preferred. These data for the pressure relate to the pressure in the quench container. The working-up of the reaction mixture can also be carried out in a cascade of two or more quench containers. Thus, the reaction mixture can first be quenched with pure water in the first container and the neutralization with a base can then be carried out in a second container. A further variant of the working-up of the reaction mixture comprises first separately condensing the steam and then crystallizing the liquid reaction product (sulfuric acid monoester) on a flaking roll or a cooling belt and recovering it as solid.

The reaction can be carried out, for example, in enameled apparatuses, ceramic or in apparatuses comprising glass or quartz glass. The particular advantage of the process according to the invention over the known processes is the enormous increase in the space-time yield, the very low energy consumption and the fact that the reaction can be carried out in the absence of diluents, such as a suspending medium. Moreover, there are no apparatus-related problems with abrasion and caking (caking of product on or in the apparatuses) in the process according to the invention.

Sulfuric acid monoesters of aminoalkanols are, for example, intermediates for the preparation of ethylenimine, which is processed, inter alia, to give polyethylenimine. Polyethylenimine is used, for example, in improving the wet strength of paper or as a retention aid in papermaking.

The stated percentages in the example are percent by weight.

EXAMPLE 1

Two capillaries having a diameter of 0.5 mm are arranged at an angle of about 90° at the top of a glass mixing chamber. A tube which has a diameter of 1 mm at this point and widens towards the end in five steps to 5 mm was present at the bottom of the mixing chamber. The end of this tube enters the top of a glass quench container. The nozzles through which the quench liquid was pumped into the container were also present here. The tube had a total length of 120 cm. It was arranged helically. Mixing chamber and helical tube were surrounded by a jacket and were present in a heat-transfer medium (oil bath) which had a temperature of 270° C. The pressure in the quench container was adjusted to 36 mbar.

4.8 ml/min of 96% strength of sulfuric acid were pumped continuously through one capillary and 5 ml/min of monoethanolamine (2-aminoethanol) were pumped continuously through the other capillary into the mixing chamber. The temperature of the two starting materials was 20° C. prior to mixing. The temperature of the reaction mixture was 270° C. At the lower end of the tube, 2-aminoethyl hydrogen sulfate (=sulfuric acid monoester of 2-aminoethanol) dropped into the quench container, in which the hot reaction mixture was quenched with a 10% strength aqueous sodium hydroxide solution. After the steady state had been reached, the quench liquid contained the sodium salt of 2-aminoethyl hydrogen sulfate and sodium hydroxide solution. The sodium hydroxide solution was then pumped with pH control to the quench liquid before the entrance into the quench container so that the quench liquid had a pH of 10.7. Aqueous solution of the sodium salt of 2-aminoethyl hydrogen sulfate was removed continuously from the bottom of the quench container by keeping the height of the quench liquid in the quench container constant. The yield was 98.9%.

EXAMPLE 2

Example 1 was repeated with the following changes: The amount of 96% strength sulfuric acid was 4.8 ml/min and the amount of monoethanolamine was 5 ml/min. The reaction was carried out at atmospheric pressure and the pH of the quench liquid was adjusted to 9.9. The yield was 88.8%.

EXAMPLE 3

Example 1 was repeated with the exceptions that a pressure of 39 mbar was established, and in each case 15 ml/min of sulfuric acid and monoethanolamine were metered into the mixing chamber and the pH of the quench liquid was adjusted to 10.8. The yield was 96.3%.

EXAMPLE 4

A reactor was used which differed from that described in example 1 only in that the mixing chamber was connected to the quench container via a straight tube having a diameter of 1 mm. 15 ml/min of 96% strength sulfuric acid and 13.9 ml/min of monoethanolamine were metered into the mixing chamber. The reaction temperature was 280° C., the pressure in the quench container was 45 mbar and the pH of the quench liquid was 10.2. The yield was 95%.

We claim:

1. A process for the preparation of sulfuric acid monoesters of aminoalkanols comprising: (a) reacting sulfuric acid with aminoalkanols and (b) removing the water forming in the reaction from the reaction mixture,
   wherein sulfuric acid and at least one aminoalkanol are mixed and the hot reaction mixture forming is passed with turbulent flow into a container and quenched therein with a fluid, wherein the temperature of said quench liquid is from −10° to 80° C.

2. The process according to claim 1, which is carried out continuously.

3. The process according to claim 1, wherein sulfuric acid and aminoalkanol are combined in a mixing chamber, the reaction mixture is passed through a tube having a diameter of at least 0.5 mm into a container, and the reaction mixture is quenched therein with an aqueous medium.

4. The process according to claim 1, wherein the reaction mixture is passed from the mixing chamber through a tube into the quench container, said tube, on entering the quench container, has a diameter which is a factor of from 2 to 1000 greater than at the exit of the mixing chamber.

5. The process according to claim 1, wherein the reaction mixture is quenched with aqueous sodium hydroxide solution.

6. The process according to claim 1, wherein the reaction mixture is quenched with an aqueous solution which comprises an alkali metal salt of a sulfuric acid monoester of an aminoalkanol and an alkali metal hydroxide.

7. The process according to claim 1, wherein the temperature in the reaction zone is at least 220° C.

8. The process according to claim 1, wherein the temperature in the reaction zone is more than 250° C.

9. The process according to claim 1, wherein sulfuric acid and at least one aminoalkanol are combined in a mixing chamber.

10. The process according to claim 1, wherein sulfuric acid and at least one aminoalkanol are combined with the aid of a multi-material nozzle.

11. The process according to claim 1, wherein the molar ratio of sulfuric acid to aminoalkanol is from 1:1.5 to 1:0.5.

12. The process according to claim 1, wherein the molar ratio of sulfuric acid to aminoalkanol is from 1:1 to 1:0.9.

13. The process according to claim 1, wherein the reaction is carried out at reduced pressure.

14. The process according to claim 1, wherein the reaction is carried out at absolute pressures of from 1 to 200 mbar.

15. The process according to claim 1, wherein the reaction is carried out at absolute pressures of from 15 to 50 mbar.

* * * * *